US009718798B2

(12) United States Patent
Browning et al.

(10) Patent No.: US 9,718,798 B2
(45) Date of Patent: Aug. 1, 2017

(54) SOLID FORMS OF 5-(HALOMETHYL)FURFURAL AND METHODS FOR PREPARING THEREOF

(71) Applicant: MICROMIDAS, INC., West Sacramento, CA (US)

(72) Inventors: Shawn M. Browning, Sacramento, CA (US); Makoto N. Masuno, Elk Grove, CA (US); John Bissell, II, Sacramento, CA (US); Benjamin F. Nicholson, Sacramento, CA (US)

(73) Assignee: MICROMIDAS, INC., West Sacramento, CA (US)

( * ) Notice: Subject to any disclaimer, the term of this patent is extended or adjusted under 35 U.S.C. 154(b) by 0 days.

(21) Appl. No.: 14/852,152

(22) Filed: Sep. 11, 2015

(65) Prior Publication Data

US 2016/0002190 A1   Jan. 7, 2016

Related U.S. Application Data

(63) Continuation of application No. PCT/US2014/024940, filed on Mar. 12, 2014.

(60) Provisional application No. 61/785,749, filed on Mar. 14, 2013.

(51) Int. Cl.
*C07D 307/18* (2006.01)
*C07D 307/46* (2006.01)
*C07D 307/48* (2006.01)

(52) U.S. Cl.
CPC ......... *C07D 307/46* (2013.01); *C07D 307/18* (2013.01); *C07D 307/48* (2013.01)

(58) Field of Classification Search
CPC ... C07D 307/46; C07D 307/48; C07D 307/18
See application file for complete search history.

(56) References Cited

U.S. PATENT DOCUMENTS

| | | | |
|---|---|---|---|
| 2,494,325 A | 1/1950 | Anne et al. | |
| 2,611,740 A | 9/1952 | Berriman et al. | |
| 4,001,283 A | 1/1977 | Wells, Jr. | |
| 4,424,390 A | 1/1984 | Hamada et al. | |
| 4,433,155 A | 2/1984 | Gilpin | |
| 4,971,657 A | 11/1990 | Avignon et al. | |
| 6,162,350 A | 12/2000 | Soled et al. | |
| 6,788,280 B2 | 9/2004 | Ham | |
| 7,173,142 B2 | 2/2007 | Steiner et al. | |
| 7,829,732 B2 | 11/2010 | Mascal | |
| 9,102,644 B2 | 8/2015 | Mikochik et al. | |
| 9,126,964 B2 | 9/2015 | Masuno et al. | |
| 9,388,150 B2 | 7/2016 | Kim et al. | |
| 9,388,151 B2 | 7/2016 | Browning et al. | |
| 2005/0032707 A1 | 2/2005 | Prasad et al. | |
| 2007/0161795 A1 | 7/2007 | Cvak et al. | |
| 2009/0234142 A1 | 9/2009 | Mascal | |
| 2010/0083565 A1 | 4/2010 | Gruter | |
| 2010/0210745 A1 | 8/2010 | McDaniel et al. | |
| 2011/0144359 A1 | 6/2011 | Heide et al. | |
| 2014/0066641 A1 | 3/2014 | Cho et al. | |
| 2014/0100378 A1 | 4/2014 | Masuno et al. | |
| 2014/0187802 A1 | 7/2014 | Mikochik et al. | |
| 2015/0203462 A1 | 7/2015 | Cahana et al. | |
| 2015/0266843 A1 | 9/2015 | Browning et al. | |
| 2016/0002191 A1 | 1/2016 | Wood et al. | |
| 2016/0168107 A1 | 6/2016 | Masuno et al. | |
| 2016/0207897 A1 | 7/2016 | Wood et al. | |

FOREIGN PATENT DOCUMENTS

| | | |
|---|---|---|
| CN | 1190979 A | 8/1998 |
| CN | 1281424 A | 1/2001 |
| CN | 101475544 A | 7/2009 |
| CN | 102066304 A | 5/2011 |
| CN | 102675265 A | 9/2012 |
| CN | 103930411 A | 7/2014 |
| CN | 104955817 A | 9/2015 |
| DE | 635783 C | 9/1936 |
| EP | 291494 A2 | 11/1988 |
| EP | 1049657 B1 | 3/2003 |
| GB | 1220851 A | 1/1971 |
| GB | 1448489 A | 9/1976 |
| RU | 2429234 C2 | 9/2011 |
| WO | 9638500 A1 | 12/1996 |
| WO | 9925675 A1 | 5/1999 |
| WO | 2009155297 A1 | 12/2009 |
| WO | 2011/161141 A1 | 12/2011 |
| WO | 2012111988 A1 | 8/2012 |
| WO | 2012170520 A1 | 12/2012 |
| WO | 2013024162 A1 | 2/2013 |
| WO | 2014066746 A1 | 5/2014 |
| WO | 2014/159741 A1 | 10/2014 |

(Continued)

OTHER PUBLICATIONS

Aho et al., "Catalytic Pyrolysis of Biomass in a Fluidized Bed Reactor: Influence of the Acidity of H-Beta Zeolite", Trans ICheme, Part B, Process Safety and Environmental Protection, vol. 85, No. B5, Sep. 2007, pp. 473-480.
Aho et al., "Catalytic Upgrading of Woody Biomass Derived Pyrolysis Vapours Over Iron Modified Zeolites in a Dual-Fluidized Bed Reactor", Fuel, vol. 89, 2010, pp. 1992-2000.
Alonso et al., "Catalytic Conversion of Biomass to Biofuels", Green Chemistry, vol. 12, No. 9, 2010, pp. 1493-1513.
Bemiller, James N., "Carbohydrates", Kirk-Othmer Encyclopedia of Chemical Technology, vol. 4, Jan. 16, 2004, pp. 696-733.
Brasholz et al., "Highly Efficient Dehydration of Carbohydrates to 5-(Chloromethyl)Furfural(CMF), 5-(Hydroxymethyl)Furfural (HMF) and Levulinic acid by Biphasic Continuous Flow Processing", Green Chemistry, vol. 13, 2011, pp. 1114-1117.

(Continued)

*Primary Examiner* — Samantha Shterengarts
*Assistant Examiner* — Matt Mauro
(74) *Attorney, Agent, or Firm* — Morrison & Foerster LLP

(57) ABSTRACT

Provided are solid forms of 5-(halomethyl)furfural, including a crystalline form of 5-(chloromethyl)furfural. Provided are also methods for preparing solid forms of 5-(halomethyl)furfural by crystallization using certain solvents.

23 Claims, 7 Drawing Sheets

(56) References Cited

FOREIGN PATENT DOCUMENTS

WO      2015023918 A2      2/2015

OTHER PUBLICATIONS

Breeden et al., "Microwave Heating for Rapid Conversion of Sugars and Polysaccharides to 5-Chloromethyl Furfural", Green Chemistry, vol. 15, 2013, pp. 72-75.
Chheda et al., "Production of 5-Hydroxymethylfurfural and Furfural by Dehydration of Biomass-Derived Mono- and Poly-Saccharides", Royal Society of Chemistry, Green Chemistry, vol. 9, 2007, pp. 342-350.
Chundury et al., "Preparation of Polymeric Building Blocks from 5-Hydroxymethyl- and 5-Chloromethylfurfuraldehyde", Industrial and Engineering Chemistry Product Research and Development, vol. 20, No. 1, 1981, pp. 158-163.
"Database WPI Week 200952", XP002684874, 4 pages.
Dunlop, A. P., "Furfural formation and Behavior", Industrial & Engineering Chemistry, vol. 40, No. 2, 1948, pp. 204-209.
Extended European Search Report (includes Supplementary European Search Report and Search Opinion) received for European Patent Application No. 14776137.3, mailed on Jul. 4, 2016, 5 pages.
Fenton et al., "LXXXV.—Derivatives of Methylfurfural", Journal of the Chemical Society, Transactions, vol. 79, 1901, pp. 807-816.
Fenton et al., "XLI.—Bromomethylfurfuraldehyde", Journal of the Chemical Society, Transactions, vol. 75, 1899, pp. 423-433.
Hamada et al., "An Improved Method for the Conversion of Saccharides into Furfural Derivative", The Chemical Society of Japan, 1982, pp. 617-618.
Haworth et al., "The Conversion of Sucrose into Furan Compounds. Part I. 5-Hydroxymethylfurfuraldehyde and Some Derivatives", Journal of the Chemical Society, 1944, pp. 667-670.
Hibbert et al., "Studies on Cellulose Chemistry II. The Action of Dry Hydrogen Bromide on Carbohydrates and Polysaccharides1,2", Journal of the American Chemical Society, vol. 45, No. 1, 1923, pp. 176-182.
Intention to Grant received for European Patent Application No. 12733249.2, mailed on Aug. 21, 2015, 7 pages.
Intention to Grant received for European Patent Application No. 12733249.2, mailed on Mar. 30, 2015, 7 pages.
International Preliminary Report on Patentability received for PCT Patent Application No. PCT/US2012/041087, mailed on Dec. 27, 2013, 8 pages.
International Preliminary Report on Patentability received for PCT Patent Application No. PCT/US2013/066788, mailed on May 7, 2015, 9 pages.
International Preliminary Report on Patentability received for PCT Patent Application No. PCT/US2014/024940, mailed on Oct. 1, 2015, 9 pages.
International Preliminary Report on Patentability received for PCT Patent Application No. PCT/US2014/024949, mailed on Sep. 24, 2015, 15 pages.
International Preliminary Report on Patentability received for PCT Patent Application No. PCT/US2014/056572, mailed on Mar. 31, 2016, 7 pages.
International Search Report & Written Opinion received for PCT Patent Application No. PCT/US2014/056572, mailed on Nov. 24, 2014, 9 pages.
International Search Report and Written Opinion received for PCT Patent Application No. PCT/US2012/041087, mailed on Oct. 19, 2012, 12 pages.
International Search Report and Written Opinion received for PCT Patent Application No. PCT/US2013/066788, mailed on Feb. 6, 2014, 11 pages.
International Search Report and Written Opinion received for PCT Patent Application No. PCT/US2014/024940, mailed on Jul. 14, 2014, 12 pages.
International Search Report and Written Opinion received for PCT Patent Application No. PCT/US2014/024949, mailed on Jul. 11, 2014, 17 pages.
International Search Report and Written Opinion received for PCT Patent Application No. PCT/US2016/022790, mailed on Jun. 3, 2016, 8 Pages.
Jin et al., "Application of Hydrothermal Reaction to Conversion of Plant-Origin Biomasses into Acetic and Lactic Acids", Journal of Materials Science, vol. 43, No. 7, Apr. 2008, pp. 2463-2471.
Kaliyan et al., "Densification Characteristics of Corn Cobs", Fuel Processing Technology, vol. 91, No. 5, May 2010, pp. 559-565.
Kumari et al., "Synthesis of 5-Bromomethylfurfural from Cellulose as a Potential Intermediate for Biofuel", European Journal of Organic Chemistry, 2011, pp. 1266-1270.
Liley, P. E., "Section 2: Physical and Chemical Data", Perry's Chemical Rngineer's Handbook, 1997, 1 page.
Liu et al., "Theoretical Studies on Thermochemistry for Conversion of 5-Chloromethylfurfural into Valuable Chemicals", The Journal of Physical Chemistry A., vol. 115, No. 46, 2011, pp. 13628-13641.
Mascal et al., "Direct, High-Yield Conversion of Cellulose into Biofuel", Angewandte Chemie International Edition, vol. 47, 2008, pp. 7924-7926.
Mascal et al., "Dramatic Advancements in the Saccharide to 5-(Chloromethyl)furfural Conversion Reaction", Chemsuschem, vol. 2, No. 9, Sep. 21, 2009, pp. 859-861.
Mascal et al., "Towards the Efficient, Total Glycan Utilization of Biomass", Chemsuschem, vol. 2, 2009, pp. 423-426.
Moye, C. J., "5-Hydroxymethylfurfural", Reviews of Pure and Applied Chemistry, vol. 14, Jan. 1964, pp. 161-170.
Nawale et al., "Synthesis and Evaluation of Novel Thiazolidinedione Derivatives for Antibacterial Activity", Der Pharma Chemica, vol. 4, No. 6, 2012, pp. 2270-2277.
Non Final Office Action received for U.S. Appl. No. 14/124,240, mailed on Aug. 14, 2014, 13 pages.
Non Final Office Action received for U.S. Appl. No. 14/124,240, mailed on Nov. 14, 2014, 13 pages.
Non-Final Office Action received for U.S. Appl. No. 14/805,321, mailed on Aug. 11, 2016, 12 pages.
Notice of Allowance received for Chinese Patent Application No. 201280028270.2, mailed on May 18, 2016, 2 pages (1 page of English Translation and 1 page of Official Copy).
Notice of Allowance received for U.S. Appl. No. 14/438,600, mailed on Nov. 12, 2015, 6 Pages.
Notice of Allowance received for U.S. Appl. No. 14/124,240, mailed on Apr. 10, 2015, 7 pages.
Notice of Allowance received for U.S. Appl. No. 14/438,600, mailed on Mar. 14, 2016, 5 pages.
Office Action Received for Chinese Patent Application No. 201280028270.2, mailed on Jan. 23, 2015, 11 pages (7 pages of English Translation and 4 pages of Official Copy).
Office Action received for Chinese Patent Application No. 201280028270.2, mailed on Oct. 10, 2015, 6 pages (3 pages of English Translation and 3 pages of Official Copy).
Office Action received for Chinese Patent Application No. 201380056131.5, mailed on Jun. 1, 2016, 14 pages (8 pages of English Translation and 6 pages of Official Copy).
Quiroz-Florentino et al., "Total Synthesis of Naturally Occurring Furan Compounds 5-{[(4-Hydroxybenzyl)Oxy]Methyl}-2-Furaldehyde and Pichiafuran C", Synthesis, No. 7, 2011, pp. 1106-1112.
Sanda et al., "The Vilsmeier Reaction: A New Synthetic Method for 5-(Chloromethyl)-2-furaldehyde", Synthesis, No. 6, Jun. 1992, pp. 541-542.
Surh et al., "5-Sulfooxymethylfurfural as a Possible Ultimate Mutagenic and Carcinogenic Metabolite of the Maillard Reaction Product, 5-Hydroxymethylfurfural", Carcinogenesis, vol. 15, No. 10, 1994, pp. 2375-2377.
Surh et al., "Activation of the Maillard Reaction Product 5-(Hydroxymethyl)furfural to Strong Mutagens via Allylic Sulfonation and Chlorination", Chemical Research in Toxicology, vol. 7, No. 3, 1994, pp. 313-318.
Szmant et al., "The Preparation of 5-Chloromethylfurfuraldehyde from High Fructose Corn Syrup and Other Carbohydrates", Journal of Chemical Technology and Biotechnology, vol. 31, No. 1, 1981, pp. 205-212.

(56) References Cited

OTHER PUBLICATIONS

Timko et al., "The Furanyl Unit in Host Compounds", Journal of the American Chemical Society, vol. 96, No. 22, Oct. 30, 1974, pp. 7159-7160.
Werther, Joachim, "Fluidized-Bed Reactors", Wiley Online Library, Ullmann's Encyclopedia of Industrial Chemistry, vol. 15, 2007, 48 pages.
Wikipedia, "1,2-Dichloroethane", available online at <https://en.wikipedia.org/wiki/1,2-Dichloroethane> on Aug. 3, 2014, Aug. 3, 2014, 4 pages.
Worden, Edward Chauncey, "Technology of Cellulose Esters", vol. 1—Part 1, 1921, p. 186.
Notice of Allowance received for U.S. Appl. No. 14/805,321, mailed on Dec. 29, 2016, 7 pages.
Notice of Allowance received for U.S. Appl. No. 14/852,306, mailed on Oct. 26, 2016, 13 pages.
Zheng, Baohui, "Synthesis of Sucrose Derivatives and Catalytic Reaction Process", Thesis for Ph.D of Nanjing University of Science and Technology, Jul. 2012, pp. 62-63 (4 pages of Foreign Language and 4 pages of English Translation).

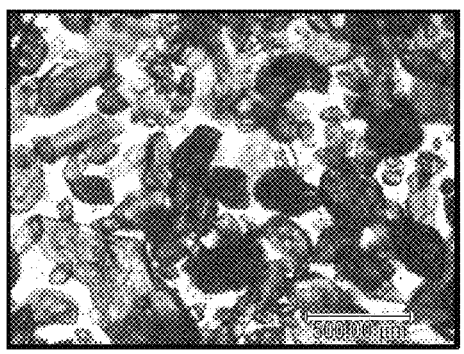
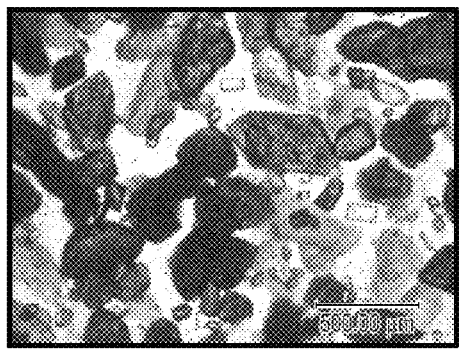
FIG. 2A  FIG. 2B
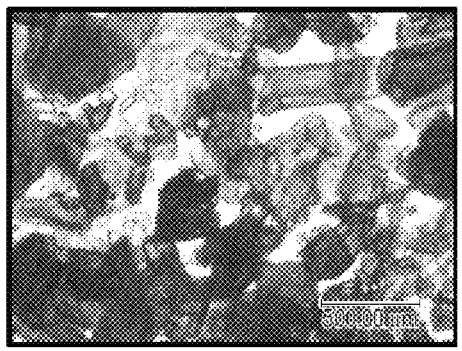
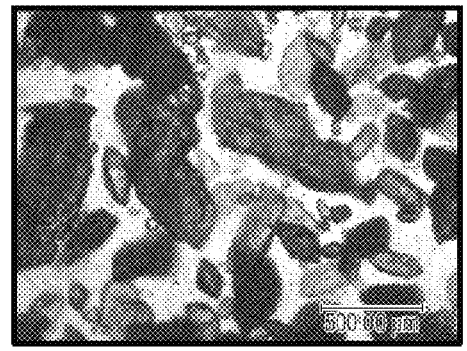
FIG. 2C  FIG. 2D

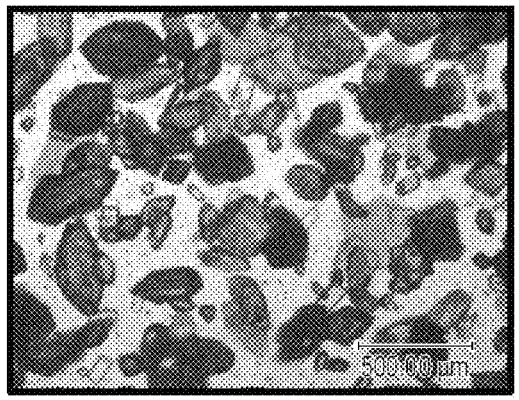
*FIG. 2E*
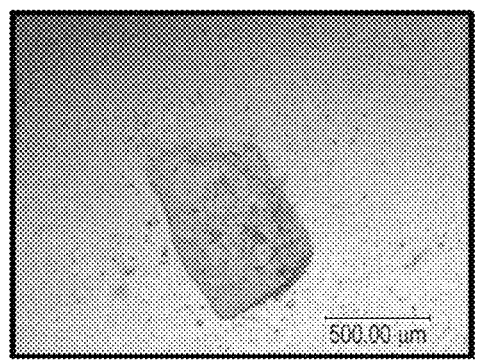 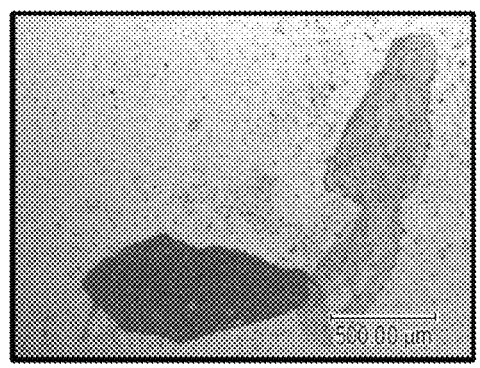
*FIG. 3A*   *FIG. 3B*

SOLID FORMS OF 5-(HALOMETHYL)FURFURAL AND METHODS FOR PREPARING THEREOF

CROSS-REFERENCE TO RELATED APPLICATION

This application is a continuation application of International Application PCT/US2014/024940, filed Mar. 12, 2014, which claims priority to and the benefit of U.S. Provisional Patent Application No. 61/785,749, filed Mar. 14, 2013, the disclosures of which are incorporated herein by reference in their entireties.

FIELD

The present disclosure relates generally to furfural compounds, and more specifically to solid forms of 5-(halomethyl)furfural, such as 5-(chloromethyl)furfural (CMF) and methods for preparing solid forms of 5-(halomethyl)furfurals.

BACKGROUND

Efforts to reduce dependence on fossil fuels for transportation fuel and as feedstock for industrial chemicals have been undertaken for decades, with a particular focus on enabling economic feasibility of renewable feedstocks. Heightened efforts are being made to more effectively utilize renewable resources and develop "green" technologies, due to continued long-term increases in the price of fuel, increased environmental concerns, continued issues of geopolitical stability, and renewed concerns for the ultimate depletion of fossil fuels.

Cellulose in biomass is commonly used as a feedstock for biofuel production. For example, cellulose can be used to produce ethanol. Cellulose can also be used to produce furan-based biofuels by way of 5-(halomethyl)furfural, such as 5-(chloromethyl)furfural (CMF). CMF can be converted into 5-(ethoxymethyl)furfural, a compound considered as a promising diesel fuel additive. Alternatively, CMF can also be converted into 5-methylfurfural, another compound considered as a promising a biofuel candidate.

The production of CMF from cellulose was first described in the early 1900s. Currently, various synthetic routes are known in the art to produce CMF. CMF is typically produced as an oily residue that can be purified by distillation. A liquid form of CMF is typically obtained from the distillation. See e.g., Szmant & Chundury, *J. Chem. Tech. Biotechnol.* 1981, 31, 205-212; Liu et al., *J. Phys. Chem. A*, 2011, 115, 13628-13641; and U.S. Pat. No. 7,829,732. The liquid CMF can then be further used in one or more of the reactions described above to produce, for example, fuels and fuel precursors.

The liquid form of CMF and other 5-(halomethyl)furfurals, however, can present several challenges on commercial scale with respect to handling, transportation and storage of the material. Thus, what is needed in the art are solid forms of 5-(halomethyl)furfurals, such as solid forms of 5-(chloromethyl)furfural, and methods of preparing such solid forms of the compounds.

BRIEF SUMMARY

Provided herein are solid forms of 5-(halomethyl)furfurals, including solid forms of 5-(chloromethyl)furfural (CMF). In one aspect, provided is a crystalline form of CMF.

In some embodiments, the crystalline form of the CMF is Form I having an X-ray diffraction (XRD) pattern that has at least peaks at about 16.6 degrees 2θ and about 27.0 degrees 2θ. In certain embodiments, the XRD pattern further has at least one additional peak at about 20.7 degrees 2θ, about 22.0 degrees 2θ, about 30.3 degrees 2θ, and about 31.1 degrees 2θ.

It should be understood that relative intensities can vary depending on a number of factors, including sample preparation, mounting, the instrument, temperature, analytical procedure, and other settings used to obtain the spectrum. As such, the peak assignments listed herein (e.g., for Form I of CMF) may, in certain embodiments, encompass variations of +/−0.5 degrees 2θ.

Form I of CMF has a single crystal X-ray diffraction pattern substantially as shown in FIG. 1. Unless otherwise stated, the single crystal X-ray diffraction pattern provided herein is generated by an X-ray diffractometer at about 90 K. Form I of CMF also has X-ray powder diffraction (XRPD) patterns substantially as shown in FIGS. 5(*a*)-(*c*). Unless otherwise stated, the XRPD pattern provided herein is generated by an X-ray diffractometer at about 320 K. In certain instances, an XRPD pattern may also be calculated from the single crystal data acquired for that form. Form I of CMF may have an X-ray diffraction pattern substantially as shown in FIG. 5(*d*). Form I is also a monoclinic crystal system, with a space group of P $2_1$/c.

Provided are also methods for preparing a solid form of 5-(halomethyl)furfural by:
a) providing 5-(halomethyl)furfural;
b) providing solvent or aqueous solution;
c) contacting the 5-(halomethyl)furfural and the solvent or aqueous solution at an elevated temperature to produce a mixture; and
d) cooling the mixture from the elevated temperature to an isolation temperature to produce a solid form of 5-(halomethyl)furfural.

In certain embodiments, the method further includes isolating the solid form of 5-(halomethyl)furfural from the cooled mixture.

In certain embodiments of the method, the 5-(halomethyl)furfural provided in step (a) above may be amorphous or non-crystalline.

In some embodiments of the method, the solvent includes one or more aromatic solvents. In certain embodiments, the solvent includes one or more alkyl phenyl solvents. In certain embodiments, the solvent includes one or more linear alkylbenzenes. In one embodiment, the solvent includes dodecylbenzene, pentylbenzene, hexylbenzene, and other alkyl benzenes (e.g., Wibaryl® A, Wibaryl® B, Wibaryl® AB, Wibaryl® F, Wibaryl® R, Cepsa Petrepar® 550-Q, Cepsa Petrepar® 900-Q, Santovac® 5, Santovac® 7), or any combinations or mixtures thereof.

In other embodiments of the method, the aqueous solution includes $H^+$, $Li^+$ and $Cl^+$.

In certain embodiments of the method, the elevated temperature is at least 30° C., or between 30° C. and 60° C. In certain embodiments, the isolation temperature is less than 10° C., or between −50° C. and 10° C. It should be understood that the isolation temperature is lower than the elevated temperature.

In certain embodiments of the method, the 5-(halomethyl)furfural provided in step (a) has a purity of less than 90%. In other embodiments of the method, the solid form of 5-(halomethyl)furfural produced in step (d) has a purity of at least 90%.

Provided is also Form I of CMF obtained by the methods described above (e.g., product obtained by the process).

Provided is also a composition that includes Form I of CMF, wherein the composition is substantially free of amorphous or non-crystalline CMF. In some embodiments of the composition, less than 10% of the composition is amorphous or non-crystalline CMF.

Provided is also a composition that includes Form I of CMF, and solvent. In some embodiments of the composition, the solvent includes one or more aromatic solvents. In certain embodiments, the solvent includes one or more alkyl phenyl solvents. In certain embodiments, the solvent includes one or more linear alkylbenzenes. In one embodiment, the solvent includes dodecylbenzene, pentylbenzene, hexylbenzene, and other alkyl benzenes (e.g., Wibaryl® A, Wibaryl® B, Wibaryl® AB, Wibaryl® F, Wibaryl® R, Cepsa Petrepar® 550-Q, Cepsa Petrepar® 900-Q, Santovac® 5, Santovac® 7), or any combinations or mixtures thereof.

Provided is also a composition that includes Form I of CMF, and aqueous solution. In certain embodiments, the aqueous solution includes $H^+$, $Li^+$ and $Cl^+$.

In some embodiments of the method or composition, the solid form of 5-(halomethyl)furfural is crystalline 5-(halomethyl)furfural. In certain embodiments, the 5-(halomethyl) furfural is CMF, wherein the CMF is crystalline (e.g. Form I as described above).

DESCRIPTION OF THE FIGURES

The present application can be understood by reference to the following description taken in conjunction with the accompanying figures.

FIGS. 2A-2E show optical microscopy (OM) images of Sample 1 from Example 5.

FIGS. 3A-3J show OM images of Sample 2 from Example 5.

DETAILED DESCRIPTION

The following description sets forth exemplary methods, parameters and the like. It should be recognized, however, that such description is not intended as a limitation on the scope of the present disclosure but is instead provided as a description of exemplary embodiments.

Crystalline Forms of 5-(Halomethyl)furfural

Provided herein are solid forms of 5-(halomethyl)furfural. Specifically, a crystalline form of 5-(chloromethyl)furfural (CMF) as detailed herein is provided, as are methods of making this crystalline form. Also provided is a crystalline form of CMF obtained by the processes (e.g. methods of making) detailed herein. Compositions that include the crystalline form of CMF are also provided.

The crystalline form provided (e.g., Form I of CMF) is characterized by a variety of solid state analytical data, including for example X-ray diffraction (XRD) or optical microscopy (OM).

Figure 1:
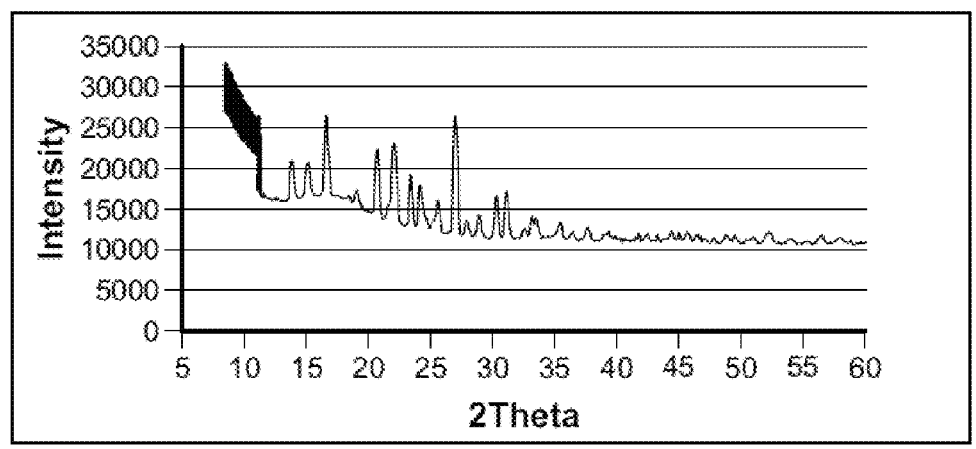
FIG. 1 shows a single crystal X-ray diffraction pattern of a crystalline form of 5-(chloromethyl)furfural (CMF), referred to herein as Form I.
Figure 3C:
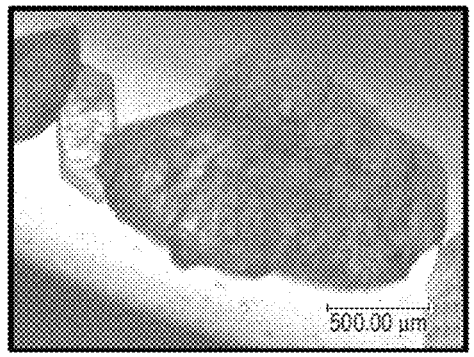
Figure 3D:
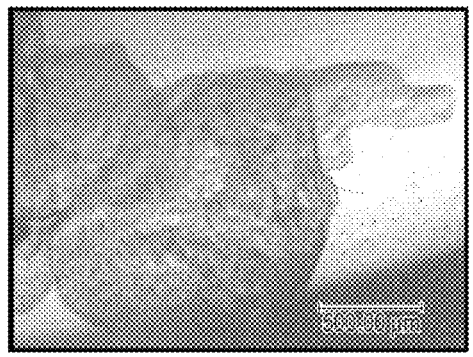
Figure 3E:
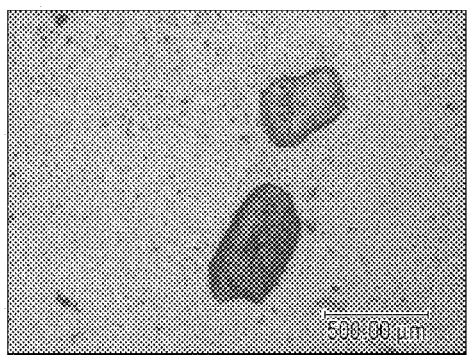
Figure 3F:
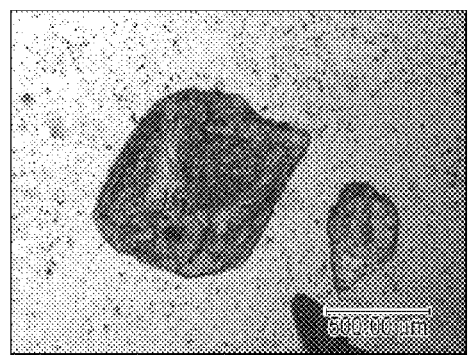
Figure 3G:
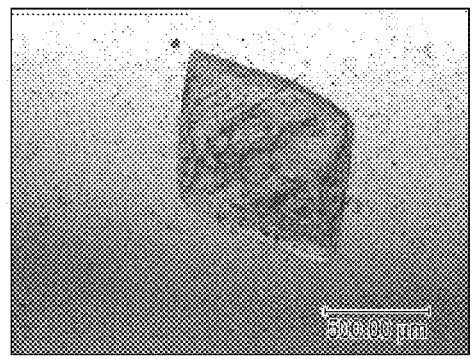
Figure 3H:
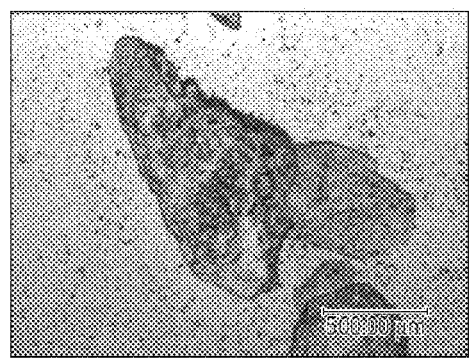
Figure 3I:
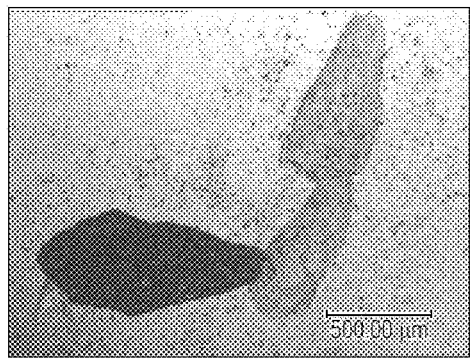
Figure 3J:
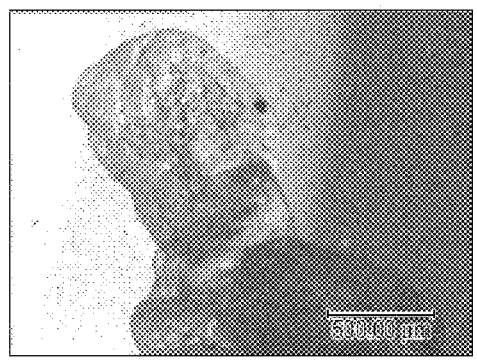
Figure 4A:
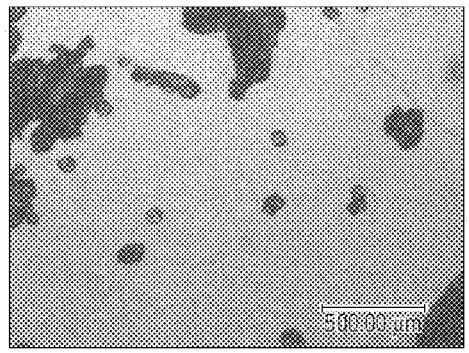
FIGS. 4A-4D show OM images of Sample 3 from Example 5.
Figure 4B:
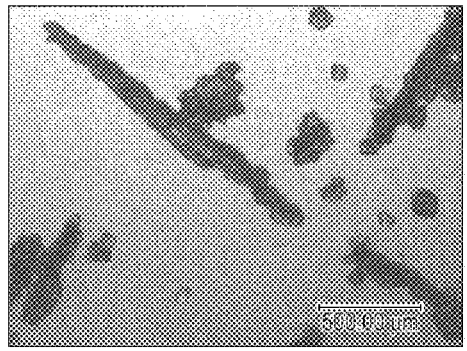
Figure 4C:
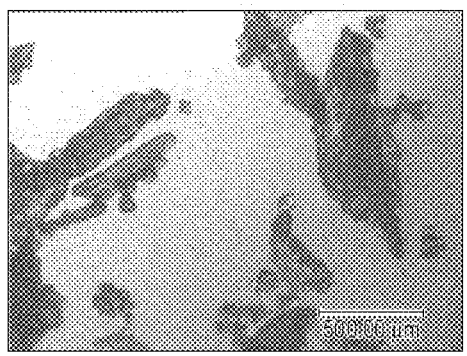
Figure 4D:
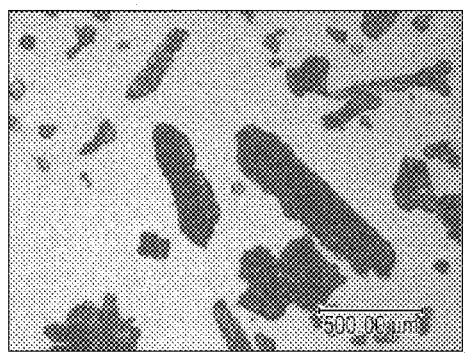

In one aspect, provided is a crystalline form of 5-(chloromethyl)furfural, wherein the crystalline form is Form I having a single crystal X-ray diffraction pattern substantially as shown in FIG. 1. The term "substantially as shown in" when referring to an XRD (such as an XRD of Form I of CMF) means that a pattern that is not necessarily identical to those depicted herein, but that falls within the limits of experimental error or deviations, when considered by one of ordinary skill in the art.

In some embodiments, Form I of CMF has an X-ray diffraction pattern displaying at least two, at least three, at least four, at least five, or at least six of the largest peaks as the single crystal X-ray diffraction pattern substantially as shown in FIG. 1.

Figure 5:
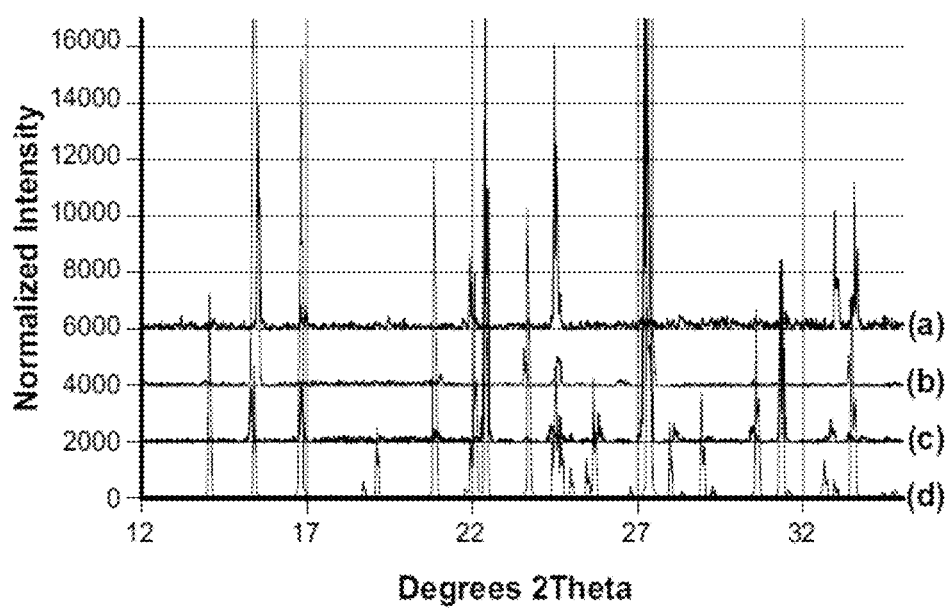
FIG. 5 shows an X-ray powder diffraction overlay of the three samples from Example 5 with the calculated powder pattern derived from the Rietveld-refined single crystal structure described in Example 2. Pattern of FIG. 5(*a*) refers to Sample 3; pattern of FIG. 5(*b*) refers to Sample 2; pattern of FIG. 5(*c*) refers to Sample 1; and pattern of FIG. 5(*d*) refers to the calculated powder pattern.

Form I of CMF may also have an X-ray powder diffraction (XRPD) pattern substantially as shown in FIG. 5(*a*), FIG. 5(*b*) or FIG. 5(*c*). In some embodiments, Form I of CMF has an X-ray diffraction pattern displaying at least two, at least three, at least four, at least five, or at least six of the largest peaks as the XRPD pattern substantially as shown in FIG. 5(*a*), FIG. 5(*b*) or FIG. 5(*c*).

In another variation, Form I of CMF has an X-ray diffraction pattern displaying at least two, at least three, at least four, at least five, or at least six of the largest peaks as the X-ray diffraction pattern calculated from a Rietveld-refined single crystal structure, wherein the pattern is substantially as shown in FIG. 5(*d*).

In some embodiments, Form I has an X-ray diffraction pattern that includes at least peaks at about 16.6 degrees 2θ and about 27.0 degrees 2θ. In certain embodiments, crystalline Form I has an X-ray diffraction pattern that further includes at least one additional peak at about 13.8 degrees 2θ, about 15.1 degrees 2θ, about 20.7 degrees 2θ, about 22.0 degrees 2θ, about 23.4 degrees 2θ, about 24.1 degrees 2θ, about 27.0 degrees 2θ, about 30.3 degrees 2θ, or about 31.1 degrees 2θ.

For example, in one embodiment, Form I of CMF has an X-ray diffraction pattern that includes at least peaks at about 16.6 degrees 2θ, about 20.7 degrees 2θ, about 27.0 degrees 2θ, about 30.3 degrees 2θ, and about 31.1 degrees 2θ. The use of the term "about" includes and describes the value or parameter per se. For example, "about x" includes and describes "x" per se. With reference to the example provided above regarding the X-ray diffraction pattern of Form I of CMF, the use of the term "about" is intended and understood to include an X-ray diffraction pattern with at least peaks at 16.6 degrees 2θ, 20.7 degrees 2θ, 27.0 degrees 2θ, 30.3 degrees 2θ, and 31.1 degrees 2θ.

It should be understood that relative intensities can vary depending on a number of factors, including sample preparation, mounting, and the instrument and analytical procedure and settings used to obtain the spectrum. As such, the peak assignments listed herein are intended to encompass variations of +/−0.5 degrees 2θ, +/−0.4 degrees 2θ, +/−0.33 degrees 2θ, +/−0.3 degrees 2θ, or +/−0.2 degrees 2θ. In other words, "about x degrees 2θ" is intended to encompass variations of +/−0.5 degrees 2θ, +/−0.4 degrees 2θ, +/−0.33 degrees 2θ, +/−0.3 degrees 2θ, +/−0.2 degrees 2θ, or +/−0.01 degrees 2θ to 0.03 degrees 2θ. In other instances, the term "about" when used in association with other measurements, or used to modify a value, a unit, a constant, or a range of values, refers to variations of +/−5%.

In some variations, Form I has a single crystal X-ray diffraction pattern that includes at least peaks (+/−0.2 degrees 2θ) at 16.6 degrees 2θ and 27.0 degrees 2θ. In certain variations, crystalline Form I has a single crystal X-ray diffraction pattern that further includes at least one additional peak (+/−0.2 degrees 2θ) at 13.8 degrees 2θ, 15.1 degrees 2θ, 20.7 degrees 2θ, 22.0 degrees 2θ, 23.4 degrees 2θ, 24.1 degrees 2θ, 27.0 degrees 2θ, 30.3 degrees 2θ, or 31.1 degrees 2θ.

In other variations, Form I has an XRPD pattern that includes at least peaks (+/−0.33 degrees 2θ) at 16.8 degrees 2θ and 27.3 degrees 2θ. In certain variations, crystalline Form I has an XRPD pattern that further includes at least one additional peak (+/−0.33 degrees 2θ) at 20.9 degrees 2θ, 22.4 degrees 2θ, or 30.4 degrees 2θ.

Form I of CMF may have at least one, at least two, at least three, or all of the following properties (i)-(iv):
  (i) crystalline Form I is a monocyclic crystal system;
  (ii) crystalline Form I has a space group P $2_1$/c;
  (iii) crystalline Form I has unit cells dimensions based on single crystal data analysis of: a=8.09(4) Å, b=8.08(2) Å, c=9.86(4) Å, α=90°, β=99.35(10°), and γ=90°; and
  (iv) crystalline Form I has a volume based on single crystal data analysis of 635.6(55) Å$^3$.

The crystal structure properties described above for Form I of CMF was collected based on the protocol described in Example 2 below. As discussed in the example, the single crystal data were collected using a diffractometer at about 90K (about −183° C.). One of skill in the art would recognize that the crystal structure properties (e.g., values for the unit cell dimensions) described above may vary slightly depending on the method, technique and/or conditions used to collect the data. For example, the values for the unit cell dimensions may vary based on the data collection temperature. In certain embodiments, the standard deviations in units of the last significant figure may be provided in parentheses.

In another variation, crystalline Form I may have at least one, at least two, at least three, or all of the following properties (i)-(iv):
  (i) crystalline Form I is a monocyclic crystal system;
  (ii) crystalline Form I has a space group P $2_1$/c;
  (iii) crystalline Form I has unit cells dimensions based on powder data analysis of: a=8.280 Å, b=8.100 Å, c=10.164 Å, α=90°, β=100°, and γ=90°; and
  (iv) crystalline Form I has a volume based on powder data analysis of 671.300 Å$^3$.

The crystal structure properties described above for Form I of CMF was collected based on the protocol described in Example 5 below. As discussed in the example, the powder data were collected using a diffractometer at about 320 K. Unless as otherwise stated, the unit cell dimensions listed herein (e.g., for Form I of CMF) may encompass variations of +/−0.0005 Å, +/−0.001 Å, or +/−0.0005 Å to 0.001 Å.

The crystalline form of CMF may also exist in various forms. For example, in some embodiments, Form I is a rhombohedral crystal, a rectangular crystal, a hexagonal crystal, a plate crystal, or an octahedral crystal, or any mixtures thereof. In one variation, Form I is a rhombohedral crystal, a rectangular crystal, or a hexagonal crystal, or any mixtures thereof. In another variation, Form I is a plate crystal or an octahedral crystal, or any mixture thereof. One of skill in the art would recognize the various methods and techniques to determine the shape of the crystals of CMF, including for example the use of optical microscopy.

Provided is also a composition including any one of the foregoing embodiments of Form I of CMF. In some embodiments, the composition is substantially free of amorphous or non-crystalline CMF. In certain embodiments, less than 20%, less 15%, less than 10%, less than 5%, less than 1%, less than 0.5%, less than 0.01%, or less than 0.05% is amorphous or non-crystalline CMF.

In other embodiments, the composition is substantially free of one or more other crystalline forms of CMF. In certain embodiments, less than 20%, less 15%, less than 10%, less than 5%, less than 1%, less than 0.5%, less than 0.01%, or less than 0.05% is one or more other crystalline forms of CMF.

Methods of Preparing Solid Forms of 5-(Halomethyl)furfural

Solid forms of 5-(halomethyl)furfural, including the crystalline forms described herein, may be prepared by crystallization of the 5-(halomethyl)furfural using certain solvents or aqueous solutions. The crystallization may also purify the 5-(halomethyl)furfural. For example, in some embodiments, the 5-(halomethyl)furfural provided for crystallization has a purity of less than 90%, less than 85%, less than 80%, less than 75%, less than 70%, less than 60%, or less than 50%. After crystallization, in certain embodiments, the solid form of 5-(halomethyl)furfural obtained from the crystallization has a purity of at least 90%, at least 95%, at least 96%, at least 97%, at least 98%, at least 99%, or at least 99.9%. Purity refers to the mass of 5-(halomethyl)furfural relative to the total mass of the sample. One of skill in the art would recognize the various methods and techniques that may be employed to determine purity of a sample.

In one aspect, provided is a method for preparing a solid form of 5-(halomethyl)furfural by: a) providing 5-(halomethyl)furfural; b) providing solvent or aqueous solution; c) contacting the 5-(halomethyl)furfural and the solvent or aqueous solution at an elevated temperature to produce a mixture; d) cooling the mixture from the elevated temperature to an isolation temperature to produce a solid form of 5-(halomethyl)furfural; and e) isolating the solid form of 5-(halomethyl)furfural from the mixture. In certain embodiments, a seed crystal of the 5-(halomethyl)furfural may be added as the mixture is being cooled or added to the cooled mixture to help with the formation of the solid form of 5-(halomethyl)furfural in the cooled mixture.

5-(Halomethyl)furfural

The 5-(halomethyl)furfural provided for crystallization may be obtained from any source (including any commercially available sources), or prepared by any suitable methods known in the art. For example, 5-(chloromethyl)furfural was first prepared by Fenton and Gostling by the action of hydrogen chloride or hydrogen bromide in ethereal solution on hexoses, sucrose and cellulose at room temperature. See Fenton & Gostling, *J. Chem. Soc.*, 1899, 75, 423. Haworth and Jones reported producing 5-(chloromethyl)furfural by passing hydrogen chloride through a suspension of aqueous sucrose in tetrachloride. See Haworth & Jones, *J. Chem. Soc.*, 1944, 667. Smantz and Chundury reported preparing 5-(chloromethyl)furfural from high fructose corn syrup and other carbohydrates using concentrated hydrochloric acid in chlorobenzene. See Szmant & Chundury, *J. Chem. Tech. Biotechnol.* 1981, 31, 205-212. More recently, Mascal described a process of preparing 5-(chloromethyl)furfural from cellulosic and hemicellulosic feedstocks using a biphasic reaction system. See U.S. Pat. No. 7,829,732; Mascal and Nikitin, *Chem Sus Chem*, 2009, 2, 859-861. Brasholz et al. also described a method of dehydrating fructose and other carbohydrates to 5-(chloromethyl)furfural using a continuous flow reactor. See Brasholz et al., *Green Chem.*, 2011, 13, 1114-1117.

Further, the 5-(halomethyl)furfural provided for crystallization may be amorphous, non-crystalline, or a form different than the form produced (i.e., before crystallization).

Elevated Temperature

In some embodiments, the 5-(halomethyl)furfural and the solvent may be contacted at an elevated temperature. In one embodiment, the elevated temperature is any temperature that is sufficient to at least partially dissolve the 5-(halomethyl)furfural in the solvent. The temperature at which the 5-(halomethyl)furfural may dissolve or partially dissolve in the solvent may vary depending on the solvent used.

In certain embodiments of the method, the 5-(halomethyl)furfural and the solvent may be combined and then heated to a temperature of at least 30° C., at least 40° C., at least 50° C., at least 60° C., at least 70° C., at least 80° C., at least 90° C., or at least 100° C.; or between 30° C. and 400° C., between 30° C. and 300° C., between 30° C. and 200° C., between 30° C. and 100° C., between 30° C. and 60° C., or between 50° C. and 250° C. to form a mixture.

In other embodiments of the method, the 5-(halomethyl)furfural, the solvent, or both may be heated at an elevated temperature, and then combined to form a mixture.

Isolation Temperature

In certain embodiments of the method, the mixture is cooled from the elevated temperature to an isolation temperature to produce the solid form of the 5-(halomethyl)furfural. The isolation temperature is any temperature lower than the elevated temperature. It should also be understood that the isolation temperature may vary depending on the solvent used.

In one embodiment, the isolation temperature is less than 10° C., less than 5° C., less than 0° C., less than −5° C., or less than −10° C., or between −50° C. and 10° C., between −50° C. and 5° C., or between −50° C. and 0° C.

Suitable methods and techniques to isolate a solid from a mixture are well known in the art. For example, the solid form of the 5-(halomethyl)furfural may be isolated from the cooled mixture by filtration.

Solvents

In some embodiments, particular solvents may be used for crystallization as described herein to obtain a solid form of 5-(halomethyl)furfural. Such solvents may be obtained from any source (including any commercially available source).

The solvent used in the methods described herein may include a single solvent or a mixture of solvents. For example, in some embodiments, the solvent may include one or more alkyl phenyl solvents, as described in further detail below. In other embodiments, the solvent may be a mixture of (i) one or more alkyl phenyl solvents, and (ii) one or more alkyl solvents. In certain embodiments, the alkyl solvents may include $C_1$-$C_{20}$ alkyl solvents (e.g., pentane, hexane, decane, and dodecane).

a) Alkyl Phenyl Solvent

As used herein, "an alkyl phenyl solvent" refers to a class of solvents that have one or more alkyl chains attached to one or more phenyl or phenyl-containing ring systems. The alkyl phenyl solvent may be referred to as an alkylbenzene or a phenylalkane. One skilled in the art would recognize that certain phenylalkanes may also be interchangeably referred to as an alkylbenzene. For example, (1-phenyl)pentane and pentylbenzene refer to the same solvent.

In some embodiments, the solvent includes an alkylbenzene. Examples may include (monoalkyl)benzenes, (dialkyl)benzenes, and (polyalkyl)benzenes. In certain embodiments, the alkylbenzene has one alkyl chain attached to one benzene ring. The alkyl chain may have one or two points of attachment to the benzene ring. Examples of alkylbenzenes with one alkyl chain having one point of attachment to the benzene ring include pentylbenzene, hexylbenzene and dodecylbenzene. In embodiments where the alkyl chain has two points of attachment to the benzene ring, the alkyl chain may form a fused cycloalkyl ring to the benzene. Examples of alkylbenzenes with one alkyl having two points of attachment to the benzene ring include tetralin. It should be understood that the fused cycloalkyl ring may be further substituted with one or more alkyl chains.

In other embodiments, the alkylbenzene has two or more alkyl chains (e.g., 2, 3, 4, 5, or 6 alkyl chains) attached to one benzene ring.

In yet other embodiments, the alkylbenzene is an alkyl-substituted fused benzene ring system. The fused benzene ring system may include benzene fused with one or more heterocyclic rings. In one embodiment, the fused benzene ring system may be two or more fused benzene rings, such as naphthalene. The fused benzene ring system may be optionally substituted by one or more alkyl chains.

In some embodiments, the solvent includes phenylalkane. Examples may include (monophenyl)alkanes, (diphenyl)alkanes, and (polyphenyl)alkanes. In certain embodiments, the phenylalkane has one phenyl ring attached to one alkyl chain. The phenyl ring may be attached to any carbon along the alkyl chain. For example, the phenyl alkyl having one alkyl chain may be (1-phenyl)pentane, (2-phenyl)pentane, (1-phenyl)hexane, (2-phenyl)hexane, (3-phenyl)hexane, (1-phenyl)dodecane, and (2-phenyl)dodecane.

In other embodiments, the phenylalkane has two or more phenyl rings attached to one alkyl chain. Suitable alkyl benzenes may include, for example, toluene, para-xylene, meta-xylene, mesitylene, Wibaryl® F (heavy alkylate), Wibaryl® A (diphenylalkanes, wherein the alkyl chains are $C_{10-13}$ alkyl chains), Wibaryl® B (dialkylbenzenes, wherein the alkyl chains are $C_{10-13}$ alkyl chains), Wibaryl® AB (a mixture of diphenylalkanes and dialkylbenzenes), Wibaryl® R (oligo- and polyalkylbenzenes), Cepsa Petrelab® 550-Q (linear alkylbenzene containing side alkyl chains of 10-13 carbon atoms), Cepsa Petrene® 900-Q (heavy alkylbenzene containing primarily dialkylbenzenes). In other embodiments, the solvent includes phenyl ethers, including monophenyl ethers, diphenyl ethers and polyphenyl ethers. Suitable phenyl ethers include, for example, Santovac® 5 and Santovac® 7.

Linear Versus Branched Solvents

"Alkyl" refers to a monoradical saturated hydrocarbon chain. The length of the alkyl chain may vary. In certain embodiments, the alkyl chain may be 1 to 20 carbon atoms (e.g., $C_{1-20}$ alkyl). In one embodiment, the alkyl chain may be 4 to 15 carbons (e.g., $C_{4-15}$ alkyl), or 10 to 13 carbons (e.g., $C_{10-13}$ alkyl).

The alkyl chain may be linear or branched. Linear alkyl chains may include, for example, n-propyl, n-butyl, n-hexyl, n-heptyl, n-octyl, n-nonanyl, n-decyl, n-undecyl, and n-dodecyl. Branched alkyl chains may include, for example, isopropyl, sec-butyl, isobutyl, tert-butyl, and neopentyl. In some embodiments where the solvent includes two or more alkyl chains, certain alkyl chains may be linear, whereas other alkyl chains may be branched. In other embodiments where the solvent includes two or more alkyl chains, all the alkyl chains may be linear or all the alkyl chains may be branched.

For example, the solvent may be a linear alkylbenzene ("LAB"). Linear alkylbenzenes are a class of solvents having the formula $C_6H_5C_nH_{2n+1}$. For example, in one embodiment, the linear alkylbenzene is dodecylbenzene. Dodecylbenzene is commercially available, and may be "hard type"

or "soft type". Hard type dodecylbenzene is a mixture of branched chain isomers. Soft type dodecylbenzene is a mixture of linear chain isomers. In one embodiment, the solvent includes hard type dodecylbenzene.

Halo-Substituted Solvents

In some embodiments, the solvent may be any of the alkyl phenyl solvents described above, in which the phenyl ring is substituted with one or more halogen atoms. In certain embodiments, the solvent includes an alkyl(halobenzene). For example, the alkyl(halobenzene) may include alkyl (chlorobenzene). In one embodiment, the halo substituent for the phenyl ring may be, for example, chloro, bromo, or any combination thereof.

b) Other Solvents

In other embodiments, the solvent may include other aromatic solvents. For example, the solvent may include benzene, naphthalene, naphthenic oil, alkylated naphthalene, anthracene, diphenyl, triphenyl methane, triphenylene, polychlorinated biphenyls, other polycyclic aromatic hydrocarbons, or other halogenated hydrocarbons.

Aqueous Solution

In other embodiments, particular aqueous solutions may be used for crystallization as described herein to obtain a solid form of 5-(halomethyl)furfural. Such aqueous solutions may be obtained from any source (including any commercially available source) or prepared according to any suitable methods known in the art.

The aqueous solution used in the methods described herein may include $H^+$, $Li^+$ and $Cl^-$. In one variation, the aqueous solution includes 2N $H^+$, 10N $Li^+$, and 12N $Cl^-$.

Enumerated Embodiments

The following enumerated embodiments are representative of some aspects of the invention.

1. A crystalline form of 5-(chloromethyl)furfural, wherein the crystalline form is Form I having an X-ray diffraction (XRD) pattern comprising at least peaks at about 16.6 degrees 2θ and about 27.0 degrees 2θ.

2. The crystalline form of embodiment 1, wherein the XRD pattern of Form I further comprises at least one additional peak at about 20.7 degrees 2θ, about 22.0 degrees 2θ, about 30.3 degrees 2θ, or about 31.1 degrees 2θ.

3. A crystalline form of 5-(chloromethyl)furfural, wherein the crystalline form is Form I having a single crystal X-ray diffraction (XRD) pattern comprising at least peaks (+/−0.2 degrees 2θ) at 16.6 degrees 2θ and 27.0 degrees 2θ.

4. The crystalline form of embodiment 3, wherein the single crystal XRD pattern of Form I further comprises at least one additional peak (+/−0.2 degrees 2θ) at 20.7 degrees 2θ, 22.0 degrees 2θ, 30.3 degrees 2θ, or 31.1 degrees 2θ.

5. A crystalline form of 5-(chloromethyl)furfural, wherein the crystalline form is Form I having a single crystal X-ray diffraction (XRD) pattern substantially as shown in FIG. 1.

6. A crystalline form of 5-(chloromethyl)furfural, wherein the crystalline form is Form I having a unit cell of the following dimensions based on single crystal data analysis:
a=8.09(4) Å;
b=8.08(2) Å;
c=9.86(4) Å;
α=90°;
β=99.35(10)°; and
γ=90°.

7. A crystalline form of 5-(chloromethyl)furfural, wherein the crystalline form is Form I having an X-ray powder diffraction (XRPD) pattern comprising at least peaks (+/− 0.33 degrees 2θ) at 16.8 degrees 2θ and 27.3 degrees 2θ.

8. The crystalline form of embodiment 7, wherein the XRPD pattern of Form I further comprises at least one additional peak (+/−0.33 degrees 2θ) at 20.9 degrees 2θ, 22.4 degrees 2θ, or 30.4 degrees 2θ.

9. A crystalline form of 5-(chloromethyl)furfural, wherein the crystalline form is Form I having an XRPD pattern substantially as shown in FIG. 5(a), FIG. 5(b) or FIG. 5(c).

10. A crystalline form of 5-(chloromethyl)furfural, wherein the crystalline form is Form I having a unit cell of the following dimensions (+/−0.001 Å) based on powder data analysis:
a=8.280 Å;
b=8.100 Å;
c=10.164 Å;
α=90°;
β=100°; and
γ=90°.

11. The crystalline form of any one of embodiments 1 to 10, wherein Form I is a monoclinic crystal system.

12. The crystalline form of any one of embodiments 1 to 11, wherein Form I has a space group of P $2_1$/c.

13. The crystalline form of any one of embodiments 1 to 12, wherein Form I is a rhombohedral crystal, a rectangular crystal, a hexagonal crystal, a plate crystal, or an octahedral crystal, or any mixtures thereof.

14. The crystalline form of embodiment 13, wherein Form I is a rhombohedral crystal, a rectangular crystal, or a hexagonal crystal, or any mixtures thereof.

15. The crystalline form of embodiment 13, wherein Form I is a plate crystal or an octahedral crystal, or any mixture thereof.

16. The crystalline form of any one of embodiments 1 to 15 obtained by:
a) providing 5-(chloromethyl)furfural;
b) providing solvent or aqueous solution;
c) contacting the 5-(chloromethyl)furfural and the solvent or aqueous solution at an elevated temperature to produce a mixture; and
d) cooling the mixture from the elevated temperature to an isolation temperature to produce the crystalline form of any one of embodiments 1 to 15.

17. The crystalline form of embodiment 16, wherein the crystalline form of any one of embodiments 1 to 15 is further obtained isolating the crystalline form from the cooled mixture.

18. The crystalline form of embodiment 16 or 17, wherein the solvent comprises one or more aromatic solvents.

19. The crystalline form of embodiment 16 or 18, wherein the solvent comprises one or more alkyl phenyl solvents.

20. The crystalline form of embodiment 16 or 19, wherein the solvent comprises one or more linear alkylbenzenes.

21. The crystalline form of embodiment 16 or 17, wherein the solvent comprises dodecylbenzene, pentylbenzene, hexylbenzene, toluene, para-xylene, meta-xylene, mesitylene, benzene, naphthalene, anthracene, triphenyl methane, triphenylene, or any combinations or mixtures thereof.

22. The crystalline form of embodiment 21, wherein the solvent comprises toluene.

23. The crystalline form of embodiment 21, wherein the solvent comprises para-xylene.

24. The crystalline form of embodiment 16 or 17, wherein the aqueous solution comprises $H^+$, $Li^+$ and $Cl^-$.

25. The crystalline form of any one of embodiments 16 to 24, wherein the elevated temperature is at least 30° C.

26. The crystalline form of any one of embodiments 16 to 25, wherein the isolation temperature is less than 10° C.

27. A composition comprising a crystalline form of 5-(chloromethyl)furfural according to any one of embodiments 1 to 26, wherein the composition is substantially free of amorphous or non-crystalline 5-(chloromethyl)furfural.

28. A composition comprising a crystalline form of 5-(chloromethyl)furfural according to any one of embodiments 1 to 26, wherein less than 10% of the composition is amorphous or non-crystalline 5-(chloromethyl)furfural.

29. A composition comprising:
   a crystalline form of 5-(chloromethyl)furfural according to any one of embodiments 1 to 26; and
   solvent or aqueous solution.

30. The composition of embodiment 29, wherein the solvent comprises one or more aromatic solvents.

31. The composition of embodiment 29, wherein the solvent comprises one or more alkyl phenyl solvents.

32. The composition of embodiment 29, wherein the solvent comprises one or more linear alkylbenzenes.

33. The composition of embodiment 29, wherein the solvent comprises dodecylbenzene, pentylbenzene, hexylbenzene, toluene, para-xylene, meta-xylene, mesitylene, benzene, naphthalene, anthracene, triphenyl methane, triphenylene, or any combinations or mixtures thereof.

34. The composition of embodiment 33, wherein the solvent comprises toluene.

35. The composition of embodiment 33, wherein the solvent comprises para-xylene.

36. The composition of embodiment 29, wherein the aqueous solution comprises $H^+$, $Li^+$ and $Cl^-$.

37. A method of preparing a solid form of 5-(halomethyl)furfural, comprising:
   a) providing 5-(halomethyl)furfural;
   b) providing solvent or aqueous solution;
   c) contacting the 5-(halomethyl)furfural and the solvent at an elevated temperature to produce a mixture; and
   d) cooling the mixture from the elevated temperature to an isolation temperature to produce a solid form of 5-(halomethyl)furfural.

38. The method of embodiment 37, further comprising isolating the solid form of 5-(halomethyl)furfural from the cooled mixture.

39. The method of embodiment 37 or 38, wherein the solvent comprises one or more aromatic solvents.

40. The method of embodiment 37 or 38, wherein the solvent comprises one or more alkyl phenyl solvents.

41. The method of embodiment 37 or 38, wherein the solvent comprises one or more linear alkylbenzenes.

42. The method of embodiment 37 or 38, wherein the solvent comprises dodecylbenzene, pentylbenzene, hexylbenzene, toluene, para-xylene, meta-xylene, mesitylene, benzene, naphthalene, anthracene, triphenyl methane, triphenylene, or any combinations or mixtures thereof.

43. The method of embodiment 42, wherein the solvent comprises toluene.

44. The method of embodiment 42, wherein the solvent comprises para-xylene.

45. The method of embodiment 37 or 38, wherein the aqueous solution comprises $H^+$, $Li^+$ and $Cl^-$.

46. The method of any one of embodiments 37 to 45, wherein the elevated temperature is at least 30° C.

47. The method of embodiment 46, wherein the elevated temperature is between 30° C. and 60° C.

48. The method of any one of embodiments 37 to 47, wherein the isolation temperature is less than 10° C.

49. The method of embodiment 48, wherein the isolation temperature is between −50° C. and 10° C.

50. The method of any one of embodiments 37 to 49, wherein the 5-(halomethyl)furfural is crystalline.

51. The method of any one of embodiments 37 to 50, wherein the 5-(halomethyl)furfural is 5-(chloromethyl)furfural.

52. The method of any one of embodiments 37 to 51, wherein the 5-(halomethyl)furfural provided in step (a) has a purity of less than 90%.

53. The method of any one of embodiments 37 to 52, wherein the solid form of 5-(halomethyl)furfural has a purity of at least 90%.

EXAMPLES

The following Examples are merely illustrative and are not meant to limit any aspects of the present disclosure in any way.

Example 1a

Preparation of CMF Crystals

This Example demonstrates the preparation of CMF crystals using dodecylbenzene (soft type). These CMF crystals were characterized in Example 2 below.

CMF (1.77 g, 99% pure) was added to a 25 mL microwave vial containing 5 mL dodecylbenzene (soft type). The temperature of the mixture was increased to 45° C. until the CMF was observed to melt. A biphase of liquid CMF and dodecylbenzene saturated with CMF was observed. The solution was allowed to cool to 29° C. A CMF seed crystal was added to the vial, and the contents of the vial were held at 29° C. overnight. After 14 hr, clear CMF crystals were observed to have formed on the bottom of the vial. The CMF crystals were stored within the supernatant.

Example 1b

Preparation of CMF Crystals

This Example demonstrates the preparation of CMF crystals using dodecylbenzene (soft type). These CMF crystals were characterized in Example 3 below.

CMF (1.44 g, 99% pure) was added to a 25 mL microwave vial containing 5 mL dodecylbenzene (soft type). The temperature of the mixture was increased to 45° C. until the CMF was observed to melt. A biphase of liquid CMF and dodecylbenzene saturated with CMF was observed. The solution was allowed to cool to 29° C. A CMF seed crystal was added to the vial, and the contents of the vial were held at 29° C. overnight. After 14 hr, clear CMF crystals were observed to have formed on the bottom of the vial. The supernatant solution (which contained dodecylbenzene (soft type) and residual dissolved CMF) was decanted and 5 mL of hexane (20° C.) was added in order to wash the CMF crystals. The hexane-wash solution was then decanted, and the wash process was repeated. The washed CMF crystals were stored in hexane (5 mL).

Example 2

Single Crystal Data for Form I of CMF

This Example demonstrates the characterization of the CMF crystals obtained from Example 1a above using single crystal data analysis.

Data were collected on a single CMF crystal obtained according to the procedure in Example 1a. A large colorless block with approximate orthogonal dimensions 0.57×0.53×0.35 mm$^3$ was placed and optically centered on the Bruker APEXII CCD diffractometer at −183° C. (~90K). The initial unit cell was indexed using a least-squares analysis of a random set of reflections collected from three series of 0.3° wide w-scans, 10 seconds per frame, and 30 frames per series that were well distributed in reciprocal space. Five w-scan data frame series were collected [MoKα] with 0.3° wide scans, 20 seconds per frame and 606 frames collected per series at varying ϕ angles (ϕ=0°, 72°, 144°, 216°, 288°), respectively. The crystal to detector distance was 5.23 cm, thus providing a complete sphere of data to $2\theta_{max}$=61.03°.

For all crystallographic calculations, a total of 12316 reflections were collected and corrected for Lorentz and polarization effects in Saint and absorption using Blessing's method as incorporated into the program SADABS with 2067 unique. The SHELXTL program package was implemented to determine the probable space group and set up the initial files. System symmetry, systematic absences and intensity statistics indicated the centrosymmetric monoclinic space group P 2$_1$/c (no. 14). The structure was determined by direct methods with the successful location of all the non-hydrogen atoms of the molecule using the program XT. The structure was refined with XL12. The 12316 data collected were merged based upon identical indices 7576 data [R(int)=0.0131], then truncated to $2\theta_{max}$=55.00° with 5512 data, and during least-squares refinement to 1462 unique data [R(int)=0.0116]. A single least-squares difference-Fourier cycle was required to locate the remaining hydrogen atoms. All non-hydrogen atoms were refined anisotropically. Hydrogen atoms were initially idealized, but then allowed to refine freely during (xyzU) during the final refinement stage. The final structure was refined to convergence with R(F)=2.81%, wR(F$_2$)=7.21%, GOF=1.138 for all 5512 unique reflections [R(F)=2.81%, wR(F$_2$)=7.21% for those 1451 data with Fo>4σ(Fo)]. The final difference-Fourier map was featureless indicating that the structure is both correct and complete. An empirical correction for extinction was also applied.

Table 1 summarizes the structural data for a single CMF crystal obtained from Example 1a above.

TABLE 1

| | |
|---|---|
| Formula weight | 144.55 |
| Temperature | 90(2) K |
| Wavelength | 0.71073 Å |
| Crystal system | Monoclinic |
| Space group | P 2$_1$/c |
| Unit cell dimensions | a = 8.0833(5) Å  α = 90° |
| | b = 8.0795(5) Å  β = 99.3360(10)° |
| | c = 9.8552(6) Å  γ = 90° |
| Volume | 635.11(7) Å$^3$ |
| Z | 4 |
| Density (calculated) | 1.512 Mg/m$^3$ |
| Absorption coefficient | 0.513 mm$^{-1}$ |
| F(000) | 296 |
| Crystal size | 0.57 × 0.53 × 0.35 mm$^3$ |
| Crystal color and habit | Colorless Block |
| Diffractometer | Bruker APEX-II CCD |
| Theta range for data collection | 2.55 to 27.50°. |
| Index ranges | −10 <= h <= 10, −10 <= k <= 10, −12 <= l <= 12 |
| Reflections collected | 5512 |
| Independent reflections | 1462 [R(int) = 0.0116] |
| Observed reflections (I > 2sigma(I)) | 1451 |

TABLE 1-continued

| | |
|---|---|
| Completeness to theta = 27.50° | 99.7% |
| Absorption correction | Semi-empirical from equivalents |
| Max. and min. transmission | 0.8416 and 0.7585 |
| Solution method | SHELXS-97 (Sheldrick, 2008) |
| Refinement method | SHELXL-97 (Sheldrick, 2008) |
| Data/restraints/parameters | 1462/0/103 |
| Goodness-of-fit on F$^2$ | 1.138 |
| Final R indices [I > 2sigma(I)] | R1 = 0.0280, wR2 = 0.0720 |
| R indices (all data) | R1 = 0.0281, wR2 = 0.0721 |
| Extinction coefficient | 0.112(6) |
| Largest diff. peak and hole | 0.404 and −0.264 e.Å$^{-3}$ |

Table 2 summarizes the atomic coordinates for a single CMF crystal obtained from Example 1a above. U(eq) is defined as one third of the trace of the orthogonalized U$^{ij}$ tensor.

TABLE 2

| | x | y | z | U(eq) |
|---|---|---|---|---|
| Cl(1) | 5138(1) | 3656(1) | 8452(1) | 22(1) |
| C(1) | 6790(1) | 3033(2) | 9829(1) | 19(1) |
| C(2) | 7320(1) | 1318(1) | 9609(1) | 15(1) |
| O(2) | 8153(1) | 1076(1) | 8524(1) | 13(1) |
| C(3) | 7183(1) | −125(2) | 10294(1) | 18(1) |
| C(4) | 7989(1) | −1356(1) | 9604(1) | 17(1) |
| C(5) | 8556(1) | −575(1) | 8542(1) | 14(1) |
| C(6) | 9485(2) | −1197(1) | 7508(1) | 17(1) |
| O(6) | 9929(1) | −357(1) | 6607(1) | 21(1) |

Table 3 summarizes the bond lengths and angles for a single CMF crystal obtained from Example 1a above.

TABLE 3

| | | | |
|---|---|---|---|
| Cl(1)—C(1) | 1.8145(12) | C(4)—C(5)—O(2) | 110.54(9) |
| C(1)—C(2) | 1.4767(15) | C(4)—C(5)—C(6) | 130.95(10) |
| C(1)—H(1A) | 0.948(16) | O(2)—C(5)—C(6) | 118.50(9) |
| C(1)—H(1B) | 0.972(16) | O(6)—C(6)—C(5) | 124.56(10) |
| C(2)—C(3) | 1.3604(16) | O(6)—C(6)—H(6) | 122.4(10) |
| C(2)—O(2) | 1.3670(13) | C(5)—C(6)—H(6) | 113.1(10) |
| O(2)—C(5) | 1.3718(13) | | |
| C(3)—C(4) | 1.4215(16) | | |
| C(3)—H(3) | 0.967(17) | | |
| C(4)—C(5) | 1.3640(16) | | |
| C(4)—H(4) | 0.953(17) | | |
| C(5)—C(6) | 1.4500(15) | | |
| C(6)—O(6) | 1.2173(14) | | |
| C(6)—H(6) | 0.972(17) | | |
| C(2)—C(1)—Cl(1) | 110.28(8) | | |
| C(2)—C(1)—H(1A) | 112.8(10) | | |
| Cl(1)—C(1)—H(1A) | 105.5(10) | | |
| C(2)—C(1)—H(1B) | 110.5(10) | | |
| Cl(1)—C(1)—H(1B) | 106.3(9) | | |
| H(1A)—C(1)—H(1B) | 111.2(14) | | |
| C(3)—C(2)—O(2) | 110.82(9) | | |
| C(3)—C(2)—C(1) | 133.02(10) | | |
| O(2)—C(2)—C(1) | 116.15(9) | | |
| C(2)—O(2)—C(5) | 106.00(8) | | |
| C(2)—C(3)—C(4) | 106.36(10) | | |
| C(2)—C(3)—H(3) | 126.3(10) | | |
| C(4)—C(3)—H(3) | 127.4(10) | | |
| C(5)—C(4)—C(3) | 106.28(10) | | |
| C(5)—C(4)—H(4) | 125.0(10) | | |
| C(3)—C(4)—H(4) | 128.7(10) | | |

Table 4 summarizes the anisotropic displacement parameters for a single CMF crystal obtained from Example 1a above. The anisotropic displacement factor exponent takes the form: $-2\Pi^2[h^2a^{*2}U^{11} + \ldots 2\ h\ k\ a^*b^*U^{12}]$.

TABLE 4

|  | $U^{11}$ | $U^{22}$ | $U^{33}$ | $U^{23}$ | $U^{13}$ | $U^{12}$ |
|---|---|---|---|---|---|---|
| Cl(1) | 22(1) | 23(1) | 21(1) | 3(1) | 3(1) | 9(1) |
| C(1) | 18(1) | 21(1) | 18(1) | −4(1) | 1(1) | 4(1) |
| C(2) | 11(1) | 20(1) | 13(1) | −2(1) | 2(1) | 1(1) |
| O(2) | 14(1) | 12(1) | 14(1) | −1(1) | 4(1) | 1(1) |
| C(3) | 14(1) | 23(1) | 16(1) | 3(1) | 2(1) | 0(1) |
| C(4) | 17(1) | 16(1) | 17(1) | 2(1) | 0(1) | −1(1) |
| C(5) | 14(1) | 12(1) | 16(1) | 0(1) | 0(1) | 1(1) |
| C(6) | 20(1) | 15(1) | 16(1) | −2(1) | 1(1) | 3(1) |
| O(6) | 27(1) | 21(1) | 17(1) | −1(1) | 6(1) | 4(1) |

Table 5 summarizes the hydrogen coordinates and isotropic displacement parameters for a single CMF crystal obtained from Example 1a above.

TABLE 5

|  | x | y | z | U(eq) |
|---|---|---|---|---|
| H(1A) | 7660(20) | 3812(19) | 9820(17) | 23(4) |
| H(1B) | 6321(19) | 3110(20) | 10675(16) | 23(4) |
| H(3) | 6660(20) | −270(20) | 11100(17) | 30(4) |
| H(4) | 8150(20) | −2500(20) | 9826(17) | 26(4) |
| H(6) | 9740(20) | −2370(20) | 7608(17) | 26(4) |

Example 3

XRD of Form I of CMF

This Example demonstrates the characterization of the CMF crystals obtained from Example 1b above using single crystal X-ray diffraction (XRD).

The CMF crystals obtained according to the procedure described in Example 1b above were characterized by single crystal X-ray diffraction (XRD). X-ray diffraction pattern was collected on a Bruker Duo diffractometer utilizing Cu radiation, with the detector set at 10 cm, 15 cm or 20 cm for increased spatial resolution, the detector set in 1024×1024 mode, and the source power set at 45 kV and 0.63 mA (~28 W). Frames were collected at 10 or 15 degree intervals, dependent upon detector distance, allowing for good spatial overlap frame to frame, with time per frame dependent upon signal to noise. Six frames were collected for the sample and then combined and integrated using Pilot software from Bruker. The XRD pattern for the CMF crystals is depicted in FIG. 1.

Example 4a

Preparation of CMF Crystals

This Example demonstrates the preparation of CMF crystals by crystallization using CEPSA 550Q in the fridge (about 7° C.). These CMF crystals were characterized in Example 5 below.

CMF was first prepared from fructose according to the following procedure. To a 500 ml threaded round bottomed flask equipped with a large egg-shaped magnetic stir bar was added 2.03 g of fructose. Concentrated HCl (20 ml) was then added and the mixture stirred at room temperature until all of the fructose had dissolved. Toluene (40 ml) was then added to the reaction vessel forming a bi-phase. The vessel was then sealed with a PTFE threaded cap and the reaction mixture stirred violently for 40 min at 60° C. The mixture was then cooled to room temperature and the contents of the flask removed and filtered over a 1.6 micron glass fiber filter with minimal suction aid. The organics were then separated from the aqueous and the aqueous subsequently washed with toluene (3×40 ml). The organics were then combined, dried over sodium sulfate, filtered, and concentrated under vacuum. The resulting CMF was then purified by kugelrohr distillation to yield 1.25 g of CMF (77% yield, 97% pure).

To a 20 ml scintillation vial was added 10 ml of CEPSA 550Q and 200 mg of the CMF prepared according to the procedure above. The mixture was slightly heated to 40° C., and CMF was observed to dissolve in the solvent. The solution was then allowed to stand in the fridge (7° C.) for 2-3 days, and crystal growth was observed. Polygonal like crystals were obtained by cooling, and isolated for further characterization.

Example 4b

Preparation of CMF Crystals

This Example demonstrates the preparation of CMF crystals by crystallization using CEPSA 550Q in the freezer (about −20° C.). These CMF crystals were characterized in Example 5 below.

CMF was prepared according to the procedure set forth in Example 4a above. To a 20 ml scintillation vial was added 10 ml of CEPSA 550Q and 200 mg of the CMF prepared according to the procedure above. The mixture was slightly heated to 40° C., and CMF was observed to dissolve in the solvent. The solution was then allowed to stand in the freezer (−20° C.) for 2-3 days, and crystal growth was observed. Needle like crystals were obtained by cooling, and isolated for further characterization.

Example 4c

Preparation of CMF Crystals

This Example demonstrates the preparation of CMF crystals by crystallization in an aqueous solution containing 2N $H^+$, 12N $Cl^-$ and 10N $Li^+$. These CMF crystals were characterized in Example 5 below.

CMF was prepared from fructose according to the procedure described in Example 4a above. To a 20 ml scintillation vial was added 10 ml of an aqueous solution containing 2N $H^+$, 12N $Cl^-$, 10N $Li^+$ and 100 mg of CMF. The mixture was slightly heated to 40° C., and CMF was observed to dissolve in the solvent. After heating, a fine suspension was obtained and was filtered through a 25 μm filter paper. The filtrated solution was allowed to stand in the freezer (about −20° C.) for about 1 week, and crystal growth was observed. Flake-like crystals were obtained, and isolated for further characterization.

Example 5

Characterization of CMF Crystals by X-Ray Powder Diffraction (XRPD) and Optical Microscopy (OM)

This Example demonstrates the characterization of the CMF crystals obtained in Examples 4a and 4b above by XRPD and OM. The samples characterized in this Example are summarized in Table 6 below.

TABLE 6

| Sample ID | Source of Sample | Description |
|---|---|---|
| 1 | Example 4a | CMF crystallization using CEPSA 550Q in the fridge (about 7° C.) |
| 2 | Example 4b | CMF crystallization using CEPSA 550Q in the freezer (about −20° C.) |
| 3 | Example 4c | CMF crystallization in an aqueous solution containing 2N $H^+$, 12N $Cl^-$ and 10N $Li^+$ |

Characterization by Optical Microscopy

Samples 1-3 were analyzed by optical microscopy. Samples were analyzed using an inverted microscope equipped with a digital camera. FIGS. 2-4 provide images of the crystals from Samples 1-3, respectively. Visual examination of the images in FIGS. 2A-2E indicated that Sample 1 had a mixture of rhombohedral, rectangular, and elongated hexagonal crystals. Visual examination of the images in FIGS. 3A-3J indicated that Sample 2 was observed to have plates and octahedral crystals. Visual examination of the images in FIGS. 4A-4D indicated that Sample 3 was observed to have bundled needles and small cuboid crystals.

Characterization by X-Ray Powder Diffraction

XRPD analysis of samples 1-3 was performed using a Rigaku Smart-Lab x-ray diffraction system configured for reflection Bragg-Brentano geometry using a line source x-ray beam. The x-ray source was a Cu Long Fine Focus tube, operated at 40 kV and 44 mA. That source provided an incident beam profile at the sample that changes from a narrow line at high angles to a broad rectangle at low angles. Beam conditioning slits were used on the line x-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. The Rigaku Smart-Lab was generally operated to give peak widths of 0.1° 2θ or less. The axial divergence of the x-ray beam was controlled by 5.0-degree Soller slits in both the incident and diffracted beam paths.

A spatula was used to isolate some of the solids and liquid from each sample 1-3. The isolated material was placed in a low background Si holder. The single crystal Si low background holder had a small circular recess that holds between 5 and 10 mg of powdered material. The test samples were then analyzed from 2 to 40 °2θ using a continuous scan of 6 °2θ per minute with an effective step size of 0.02 °2θ. Table 7 below also provides the peak assignments for Samples 1-3.

TABLE 7

Peak Assignments for Samples 1-3 (values in table expressed as degrees 2θ)

| Sample 1 | Sample 2 | Sample 3 | Peak Variation (3.3 sigma) |
|---|---|---|---|
| 15.302 | 15.48 | 15.513 | 0.30 |
| 16.813 | | 16.79 | 0.04 |
| | | 16.96 | |
| 20.886 | 21.01 | | 0.20 |
| | | 21.93 | |
| 22.43 | | 22.42 | 0.10 |
| 23.58 | 23.58 | | |
| 24.35 | | | |
| 24.51 | 24.58 | 24.51 | 0.14 |
| 24.65 | | | |
| 25.8 | | | |
| | 26.4 | | |
| 27.26 | 27.46 | 27.36 | 0.33 |
| 28.1 | | 28.26 | 0.26 |
| 29.1 | | | |
| 30.41 | 30.48 | 30.52 | 0.15 |
| 31.318 | | | |
| 32.83 | | | |
| | | 32.94 | |
| 33.36 | 33.37 | | 0.02 |
| | | 35.53 | |
| 34.49 | | | |
| | 34.75 | | |

Additionally, in order to estimate the ambient unit cell, a Rietveld refinement method was used with lattice parameters constrained to lie within typical thermal expansion ranges; which is less than 10% change from the original parameter determined at 90K. Table 8 shows the unit cell parameters at 90 K and 320 K as well as the percent change in each of the lattice parameters.

TABLE 8

Unit Cell Parameters for 90 K and 320 K Using Rietveld Refinement

| Parameters | 90 K Single Crystal | 320 K Refined Structure | % Change |
|---|---|---|---|
| Symmetry | Monoclinic P21/c | Monoclinic P21/c | — |
| a-parameter (Å) | 8.083 | 8.280 | 2.43 |
| b-parameter (Å) | 8.080 | 8.100 | 0.25 |
| c-parameter (Å) | 9.855 | 10.164 | 3.13 |
| β-parameter | 99.336 | 100.000 | 0.67 |
| Volume (Å$^3$) | 635.100 | 671.300 | 5.70 |

Using a low pass digital filter, the diffuse, or non-crystalline, liquid response was removed from the patterns for each of Samples 1-3. This results in analytical powder patterns containing only crystalline diffraction peaks. An overlay of these patterns is presented in FIGS. 5(a)-(c). Additionally, FIG. 5(d) shows a comparison between the calculated powder pattern derived from the Rietveld-refined single crystal structure described in Example 2 above (pattern d) and the observed crystalline diffraction patterns for Samples 1-3 (patterns c-a, respectively).

Comparative Example

Preparation of CMF

This Example explores the preparation of CMF from fructose. To a 500 ml tear-drop flask was added fructose (51 g, 283 mmol) and anhydrous diethylether (250 ml). The flask was then submerged into a brine/ice water bath and allowed to equilibrate to temperature. A gas sparge stone adapter was then connected to the reaction flask and anhydrous hydrogen chloride was slowly dispersed into the solution. The gas addition was monitored by the outlet via pH paper followed by bubbling through a saturated bicarbonate water bath.

After coming to saturation (or near saturation) the flask was removed from the low temperature bath and the gas adapter was replaced by a balloon. The flask was allowed to sit with occasional stirring.

About 3 days later, the organics were decanted from the now black solids, and the reaction flask was washed with excess ether. The combined organics were then neutralized in a 2 L flask first with concentrated bicarbonate solution followed by addition of solid sodium bicarbonate. The resulting organics were then decanted and the aqueous slurry was extracted with ether. The combined organics were then dried over calcium chloride in a 1 L amber for 2 days. The formation of CMF was confirmed by thin layer chromatography with comparison with a standard (commercially available source of CMF). The organics were filtered from the calcium chloride and distilled off at room temperature under reduced pressure.

Hot hexane was then added to the organic residue, forming a bi-phase (hexane on top, red oil on the bottom). The mixture was then mixed by swirling for a few seconds, and the hexane layer was isolated and cooled in the refrigerator at about 4-5° C. A red oil bi-phase was observed, which turned black over a couple of days. No crystallized product was observed by cooling in a fridge.

What is claimed is:

1. A composition comprising:
   a crystalline form of 5-(chloromethyl)furfural, wherein the crystalline form is Form I having an X-ray diffraction (XRD) pattern comprising at least peaks at about 16.6 degrees 2θ and about 27.0 degrees 2θ; and
   one or more alkyl phenyl solvents.

2. The composition of claim 1, wherein one or more of the alkyl phenyl solvents are linear alkylbenzenes.

3. The composition of claim 1, wherein one or more of the alkyl phenyl solvents are selected from the group consisting of dodecylbenzene, pentylbenzene, and hexylbenzene, or any combinations or mixtures thereof.

4. The composition of claim 1, wherein the XRD pattern of Form I further comprises at least one additional peak at about 20.7 degrees 2θ, about 22.0 degrees 2θ, about 30.3 degrees 2θ, or about 31.1 degrees 2θ.

5. The composition of claim 1, wherein Form I is a monoclinic crystal system.

6. The composition of claim 1, wherein less than 20% of the composition is amorphous 5-(chloromethyl)furfural.

7. The composition of claim 1, wherein less than 10% of the composition is amorphous 5-(chloromethyl)furfural.

8. The composition of claim 1, wherein less than 1% of the composition is amorphous 5-(chloromethyl)furfural.

9. The composition of claim 1, wherein one or more of the alkyl phenyl solvents have one alkyl chain attached to one benzene ring.

10. The composition of claim 1, wherein one or more of the alkyl phenyl solvents have two or more alkyl chains attached to one benzene ring.

11. The composition of claim 1, wherein one or more of the alkyl phenyl solvents comprise an alkyl-substituted fused benzene ring system.

12. The composition of claim 1, wherein one or more of the alkyl phenyl solvents have two or more phenyl rings attached to one alkyl chain.

13. A composition comprising:
    a crystalline form of 5-(chloromethyl)furfural, wherein the crystalline form is Form I having an X-ray diffraction (XRD) pattern substantially as shown in FIG. 1; and
    one or more alkyl phenyl solvents.

14. The composition of claim 13, wherein Form I is a monoclinic crystal system.

15. The composition of claim 13, wherein less than 20% of the composition is amorphous 5-(chloromethyl)furfural.

16. The composition of claim 13, wherein less than 10% of the composition is amorphous 5-(chloromethyl)furfural.

17. The composition of claim 13, wherein less than 1% of the composition is amorphous 5-(chloromethyl)furfural.

18. The composition of claim 13, wherein one or more of the alkyl phenyl solvents are linear alkylbenzenes.

19. The composition of claim 13, wherein one or more of the alkyl phenyl solvents are selected from the group consisting of dodecylbenzene, pentylbenzene, and hexylbenzene, or any combinations or mixtures thereof.

20. The composition of claim 13, wherein one or more of the alkyl phenyl solvents have one alkyl chain attached to one benzene ring.

21. The composition of claim 13, wherein one or more of the alkyl phenyl solvents have two or more alkyl chains attached to one benzene ring.

22. The composition of claim 13, wherein one or more of the alkyl phenyl solvents comprise an alkyl-substituted fused benzene ring system.

23. The composition of claim 13, wherein one or more of the alkyl phenyl solvents have two or more phenyl rings attached to one alkyl chain.

* * * * *